(12) United States Patent
Sonis (10) Patent No.: US 6,841,578 B2
(45) Date of Patent: Jan. 11, 2005

(54) TREATMENT AND PREVENTION OF MUCOSITIS IN CANCER PATIENTS

(76) Inventor: Stephen T. Sonis, Eight Decatur La., Wayland, MA (US) 01778

( * ) Notice: Subject to any disclaimer, the term of this patent is extended or adjusted under 35 U.S.C. 154(b) by 0 days.

(21) Appl. No.: 10/222,539

(22) Filed: Aug. 16, 2002

(65) Prior Publication Data

US 2003/0064913 A1 Apr. 3, 2003

Related U.S. Application Data

(60) Provisional application No. 60/352,674, filed on Jan. 29, 2002, and provisional application No. 60/313,081, filed on Aug. 16, 2001.

(51) Int. Cl.[7] ............................................. A61K 31/45
(52) U.S. Cl. ....................................... 514/728; 514/724
(58) Field of Search ................................. 514/724, 728

(56) References Cited

U.S. PATENT DOCUMENTS

| | | | |
|---|---|---|---|
| 5,496,828 A | 3/1996 | Cullinan | 514/324 |
| 5,891,924 A | 4/1999 | Aggarwal | 514/679 |
| 5,916,910 A | 6/1999 | Lai | 514/423 |
| 6,274,601 B1 | 8/2001 | Cullinan | 514/324 |
| 2001/0011097 A1 | 8/2001 | Sonis et al. | |

OTHER PUBLICATIONS

Moghadam B. K, et al., "Autoimmune progesterone dermatitis and stomatitis.", Abstract from Oral Surgery, Oral Medicine, Oral Pathology, Oral Radiology and Endodontics, 85(5), pp. 537–541, May 1998.*

Goldberg, et al., "Direct Injection Gas Chromatographic Mass Spectrometric Assay for *trans*–Resveratrol", Anal. Chem. 66 (1994) p. 3959–3963.

Jeandet et al., "The Production of Resveratrol (3,5,4'–trihydroxystilbene) by Grape Berries in Different Developmental Stages", Am. J. Enol. Vitic. 42 (1991) p. 41–46.

Manna, et al., "Resveratrol Suppresses TNF–Induced Activation of Nuclear Transcription Factors NF–κB, Activator Protein–1, and Apoptosis: Potential Role of Reactive Oxygen Intermediates and Lipid Peroxidation", J. Immunol. 164 (2000) p. 6509–6519.

Mohan, et al., "The Neurohormone Melatonin Inhibits Cytokine, Mitogen and Ionizing Radiation Induced NF–κB", Biochem. Mol. Biol. Int. 37 (1995) p. 1063–70.

Stojanovic; et al., "Efficiency and Mechanism of the Antioxidant Action of *trans*–Resveratrol and its Analogues in the Radical Liposome Oxidation", Arch. Biochem. Biophy. 391 (201) p. 79–89.

Database HCAPLUS on STN, No. 2002:598692, Takeuchi et al. Nuclear Factor–kappa B and TNF.–alpha. Mediate Gastric Ulceration Induced by Pharbol Myristate Acetate, abstract, Digestive Diseases and Sciences, Apr. 2002, 47(9), 2070–2078.

* cited by examiner

Primary Examiner—Dwayne Jones
(74) Attorney, Agent, or Firm—Clark & Elbing LLP (57) ABSTRACT

The invention features a method for the treatment or prevention of mucositis in an individual undergoing or preparing to undergo cancer treatment. The method includes administering a therapeutically effective amount of an inhibitor of NF-κB to an individual undergoing or preparing to undergo a treatment for cancer. In certain embodiments, the inhibitor is a compound having the formula:

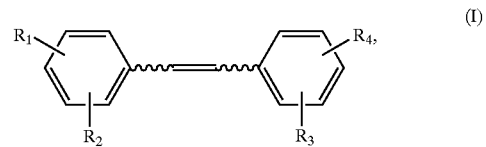

where $R_1$ and $R_4$ are OH, and $R_2$ and $R_3$ are independently OH or H, provided that when $R_1$ and $R_2$ are both OH, $R_1$ and $R_2$ cannot be disposed ortho to one another, and when $R_3$ and $R_4$ are both OH, $R_3$ and $R_4$ cannot be disposed ortho to one another. The compounds of formula I may be cis or trans.

12 Claims, 4 Drawing Sheets

| Group | Days >=3 | Days<3 | Total Days | % Days >=3 | Chi Sq v Control | P Value |
|---|---|---|---|---|---|---|
| Water Control | 81 | 95 | 176 | 46.0 | --- | --- |
| 1 mM Resveratrol, ip | 38 | 138 | 176 | 21.6 | 19.139 | <0.001 |
| 5 mM Resveratrol, ip | 48 | 106 | 154 | 31.2 | 7.000 | 0.008 |

FIG. 3

| Group | Animal | 6 | 8 | 10 | 12 | 14 | 16 | 18 | 20 | 22 | 24 | 26 |
|---|---|---|---|---|---|---|---|---|---|---|---|---|
| 1 | 1 | 0 | 2 | 3 | 4 | 4 | 4 | 3 | 2 | 2 | 2 | 2 |
|   |   | 0 | 2 | 3 | 4 | 4 | 4 | 4 | 2 | 2 | 2 | 2 |
| 1 | 2 | 1 | 0 | 1 | 1 | 3 | 3 | 3 | 3 | 2 | 2 | 3 |
|   |   | 1 | 0 | 1 | 1 | 3 | 3 | 3 | 3 | 1 | 1 | 2 |
| 1 | 3 | 1 | 0 | 2 | 2 | 3 | 3 | 3 | 3 | 3 | 3 | 3 |
|   |   | 1 | 0 | 2 | 2 | 3 | 3 | 3 | 3 | 3 | 3 | 3 |
| 1 | 4 | 1 | 0 | 1 | 2 | 3 | 3 | 3 | 3 | 3 | 3 | 3 |
|   |   | 1 | 0 | 1 | 2 | 3 | 3 | 3 | 3 | 3 | 3 | 3 |
| 1 | 5 | 0 | 0 | 2 | 2 | 3 | 3 | 3 | 3 | 2 | 1 | 1 |
|   |   | 0 | 0 | 2 | 2 | 3 | 3 | 3 | 3 | 1 | 1 | 1 |
| 1 | 6 | 1 | 2 | 2 | 3 | 3 | 3 | 3 | 2 | 2 | 1 | 1 |
|   |   | 1 | 2 | 2 | 3 | 4 | 3 | 3 | 2 | 1 | 1 | 1 |
| 1 | 7 | 1 | 0 | 1 | 2 | 3 | 2 | 2 | 1 | 1 | 1 | 1 |
|   |   | 1 | 0 | 1 | 2 | 3 | 2 | 2 | 1 | 1 | 1 | 1 |
| 1 | 8 | 1 | 0 | 1 | 3 | 3 | 3 | 3 | 3 | 3 | 3 | 3 |
|   |   | 1 | 0 | 1 | 3 | 4 | 3 | 3 | 3 | 3 | 3 | 3 |
| 2 | 9 | 1 | 0 | 1 | 2 | 3 | 3 | 3 | 1 | 3 | 1 | 1 |
|   |   | 1 | 0 | 1 | 2 | 4 | 3 | 3 | 1 | 3 | 1 | 1 |
| 2 | 10 | 0 | 1 | 2 | 3 | 3 | 2 | 1 | 1 | 1 | 1 | 1 |
|   |   | 0 | 1 | 2 | 3 | 3 | 2 | 1 | 1 | 1 | 1 | 1 |
| 2 | 11 | 0 | 0 | 0 | 2 | 3 | 4 | 3 | 3 | 3 | 2 | 1 |
|   |   | 0 | 0 | 0 | 2 | 3 | 4 | 3 | 4 | 3 | 2 | 1 |
| 2 | 12 | 0 | 0 | 0 | 2 | 3 | 3 | 3 | 1 | 1 | 1 | 1 |
|   |   | 0 | 0 | 0 | 2 | 3 | 3 | 3 | 1 | 1 | 1 | 1 |
| 2 | 13 | 0 | 0 | 0 | 2 | 3 | 3 | 3 | 1 | 1 | 1 | 1 |
|   |   | 0 | 0 | 0 | 2 | 3 | 3 | 3 | 1 | 1 | 1 | 1 |
| 2 | 14 | 0 | 0 | 2 | 2 | 3 | 2 | 2 | 1 | 1 | 1 | 1 |
|   |   | 0 | 0 | 2 | 2 | 3 | 1 | 2 | 2 | 1 | 1 | 1 |
| 2 | 15 | 0 | 1 | 0 | 2 | 1 | 2 | 1 | 1 | 1 | 1 | 1 |
|   |   | 0 | 1 | 0 | 2 | 1 | 2 | 1 | 1 | 1 | 1 | 1 |
| 2 | 16 | 2 | 0 | 2 | 3 | 1 | 1 | 1 | 1 | 1 | 1 | 1 |
|   |   | 2 | 0 | 2 | 3 | 1 | 1 | 1 | 1 | 1 | 1 | 1 |
| 3 | 17 | 0 | 0 | 0 | 2 | 3 | 3 | 3 | 3 | 3 | 2 | 1 |
|   |   | 0 | 0 | 0 | 2 | 3 | 3 | 3 | 3 | 3 | 2 | 1 |
| 3 | 18 | 0 | 0 | 2 | 3 | 3 | 3 | 2 | 1 | 1 | 1 | 2 |
|   |   | 0 | 0 | 2 | 3 | 3 | 3 | 2 | 1 | 1 | 1 | 1 |
| 3 | 19 | 0 | 0 | 1 | 2 | 3 | 3 | 3 | 3 | 2 | 2 | 2 |
|   |   | 0 | 0 | 1 | 2 | 3 | 3 | 3 | 3 | 1 | 1 | 1 |
| 3 | 20 | 0 | 2 | 2 | 3 | 3 | 3 | 2 | 3 | 3 | 1 | 2 |
|   |   | 0 | 2 | 2 | 3 | 3 | 3 | 2 | 3 | 3 | 1 | 1 |
| 3 | 21 |   |   |   |   |   |   |   |   |   |   |   |
|   |   |   |   |   |   |   |   |   |   |   |   |   |
| 3 | 22 | 0 | 0 | 0 | 2 | 2 | 3 | 1 | 1 | 1 | 1 | 1 |
|   |   | 0 | 0 | 0 | 2 | 2 | 3 | 2 | 1 | 1 | 1 | 1 |
| 3 | 23 | 0 | 0 | 1 | 2 | 2 | 3 | 3 | 3 | 1 | 1 | 1 |
|   |   | 0 | 0 | 1 | 2 | 2 | 3 | 3 | 3 | 1 | 1 | 1 |
| 3 | 24 | 0 | 0 | 0 | 2 | 3 | 3 | 3 | 1 | 1 | 1 | 1 |
|   |   | 0 | 0 | 0 | 2 | 3 | 3 | 3 | 1 | 1 | 1 | 1 |

FIG. 4

TREATMENT AND PREVENTION OF MUCOSITIS IN CANCER PATIENTS

CROSS-REFERENCE TO RELATED APPLICATIONS

The application claims benefit of priority from U.S. Provisional Application No. 60/352,674, filed Jan. 29, 2002 and U.S. Provisional Application No. 60/313,081, filed Aug. 16, 2001, each of which is hereby incorporated by reference.

BACKGROUND OF THE INVENTION

The invention relates to the field of treatment and prevention of disease.

Oral ulcerative mucositis is a common, painful, dose-limiting side effect of drug and radiation therapy for cancer. The disorder is characterized by breakdown of the oral mucosa, which results in the formation of ulcerative lesions. The lesions that result cause inflammatory and ulcerative changes that result in pain and loss of function. Consequently, patients with mucositis often require an alteration in their diets and medication to manage pain. In addition, the presence of mucositis also influences other health and economic outcomes such as medication use, febrile days, use of total parenteral nutrition, length of hospital stay, and total hospital charges. The risk of mucositis often influences the choice of drug and dose to be used in the treatment of a patient and may preclude what is considered to be the optimum anti-cancer regimen. Patients who receive myeloablative therapy are at risk for local and systemic infection. Since the mouth is rich in indigenous microbiota, the loss of mucosal integrity associated with mucositis provides a portal of entry for invading bacteria at a time when a patient's resistance to infection is highly compromised because of chemotherapy-induced neutropenia. In fact, the mouth is the most frequently identified site of origin of systemic infection among granulocytopenic cancer patients.

Mucositis occurs to some degree in more than one third of all patients receiving anti-neoplastic drug therapy. The frequency and severity are significantly greater among patients who are treated with induction therapy for leukemia or with many of the conditioning regimens for bone marrow transplant. Among these individuals, moderate to severe mucositis (ulceration) is common in more than three-quarters of patients.

Patients who receive radiation therapy for tumors of the head and neck are also at high risk for oral mucositis. The frequency and severity of mucosal injury is a function of the total amount of radiation, the schedule of radiation delivery, and the concomitant use of chemotherapy. Increasing the rate of radiation exposure results in a higher incidence of mucositis. While the increasing trend of adding chemotherapy to the radiation regimen results in an improved tumor outcome, many of these protocols are highly stomatotoxic. Mucositis is often of such severity as to necessitate a break in treatment to allow the oral tissues to recover. Such interruptions reduce the overall effectiveness of therapy.

Clinically mucositis progresses through four stages:

1. An initial stage which is characterized by inflammatory changes of erythema and edema. Localized islands of hyperkeratosis may also been seen. This stage is symptomatically mild and may be successfully palliated by topical anesthetics.
2. Subsequently the mucosa breaks down and becomes eroded and atrophic with increasingly significant inflammatory changes. This stage is increasingly painful and may require systemic analgesic therapy in the form of NSAIDs or oral narcotics for adequate palliation.
3. The third stage of mucositis is the most symptomatic. Full thickness ulcers of the mucosa cause severe discomfort necessitating parenteral narcotic therapy. In addition, in the myelosuppressive patient, these ulcerations provide a systemic portal of entry for the oral microflora often leading to bacteremia and sepsis. Antimicrobial intervention is then required.
4. Finally, spontaneous healing occurs about 2–3 weeks after cessation of anti-neoplastic therapy.

Historically mucositis was viewed as a process that was the sole result of epithelial damage. It was believed that the non-specific toxic effects of chemotherapy or radiation caused DNA damage to the rapidly dividing cells of the mucosal basal epithelium. This resulted in cell death, atrophic changes in the mucosa, and ulceration. However, four lines of observation suggested a biologic complexity that extended beyond an epithelial etiology. First, electron microscopic studies demonstrated damage to the endothelium and connective tissue that significantly preceded epithelial breakdown. Second, peripheral blood levels of pro-inflammatory cytokines increased proportionately when non-hematologic toxicities were observed. Third, attenuation of pro-inflammatory cytokine production and expression resulted in the amelioration of experimental mucositis. And fourth, alteration of the local environment by reducing its bacterial load and maintaining salivary function reduced the severity of mucositis.

The condition appears to represent a sequential interaction of oral mucosal cells and tissues including connective tissue, endothelium, epithelium, and inflammatory cells, pro-inflammatory cytokines, and local environmental factors such as bacteria and saliva. Damage to epithelial and connective tissue induces the release of inflammatory cytokines leading to mucosal damage. Additionally, both direct and indirect effects on epithelial cells result in either apoptotic or necrotic changes of basal epithelial cells; differentiation into new epithelial cells is halted. The arrest of epithelial cell renewal leads to atrophy followed by ulceration.

The findings appear to represent 'downstream' events, which result as a consequence of activation of at least two primary pathways: the transcription factor NF-κB and the ceramide pathway. It appears that reactive oxygen species (free radicals) generated by either chemotherapy or radiation are capable of initiating activation of both of these pivotal pathways in leading to mucositis.

Standard therapy for mucositis is predominantly palliative, including application of topical analgesics such as lidocaine and/or systemic administration of narcotics and antibiotics. Currently, there is no approved treatment for mucositis. There is, thus, a need for a method for treating and preventing mucositis.

SUMMARY OF THE INVENTION

The invention provides a method for the treatment or prevention of mucositis in an individual undergoing or preparing to undergo cancer treatment.

In one aspect, the invention features a method for the treatment or prevention of mucositis including administering a therapeutically effective amount of an inhibitor of NF-κB to an individual undergoing or preparing to undergo a treatment for cancer. In preferred embodiments, the treatment for cancer is radiation therapy or chemotherapy. In another embodiment, the mucositis is of the gastrointestinal tract, e.g., of the mouth, esophagus, or stomach. In other preferred embodiments, the inhibitor is administered topically, e.g., as a rinse, troche, or gel. In yet other embodiments, the inhibitor is administered orally or by intraperitoneal injection. Preferably, the inhibitor is administered in a pharmaceutically acceptable carrier, e.g., physiological saline or sterilized water.

In preferred embodiments, the inhibitor is a compound having the formula:

(I)

where $R_1$ and $R_4$ are OH, and $R_2$ and $R_3$ are independently OH or H, provided that when $R_1$ and $R_2$ are both OH, $R_1$ and $R_2$ cannot be disposed ortho to one another, and when $R_3$ and $R_4$ are both OH, $R_3$ and $R_4$ cannot be disposed ortho to one another. The compounds of formula I may be cis or trans.

In other embodiments, the inhibitor is selected from the group consisting of resveratrol, lactacystin, epigallocatechin, curcumin, pyrrolidine dithiocarbamate, herbamycin A, idoxifene, raloxifene, droloxifene, tiremifene, and tamoxifen. Preferably, inhibitors are administered in substantially pure form.

A combination of two or more inhibitors or an inhibitor and another agent, e.g., an analgesic or antibiotic, may also be administered in the methods described herein.

By "treatment" is meant the medical management of a patient with the intent that a cure, stabilization, or amelioration of mucositis will result.

By "prevention" is meant the medical management of a patient with the intent that the patient does not develop mucositis or develops mucositis with reduced severity.

By "therapeutically effective amount" is meant an amount sufficient to produce a preventative, healing, curative, stabilizing, or ameliorative effect.

By "inhibition of NF-κB" is meant inhibition of the activation or action of NF-κB. Inhibition occurs, for example, by blocking activation of NF-κB by reactive oxygen species, by inhibiting proteolysis of the ankyrin repeats in NF-κB, by blocking binding of activated NF-κB to DNA, by blocking transport of NF-κB to the nucleus, by promoting removal of NF-κB from the nucleus, by blocking phosphorylation or degradation of IκB proteins, by upregulating or increasing the concentration of IκB proteins, by inhibiting proteasome degradation of IκB proteins, by inhibiting proteasome modification of NF-κB proteins, or by downregulating or decreasing the concentration of NF-κB.

DETAILED DESCRIPTION OF THE INVENTION

Resveratrol (trans-3,4',5-trihydroxystilbene) can be used therapeutically to attenuate mucositis, as disclosed in U.S. Application Ser. No. 60/313,081, hereby incorporated by reference. Resveratrol is a polyphenolic phytoalexin that is found in grapes, fruits, and root extracts of the weed Polygonum cuspidatum. Resveratrol is isolated from grapes predominantly in the trans form. It is a non-flavinoid polyphenol that demonstrates a number of biologic activities including being anti-inflammatory, an anti-oxidant, modulating cell growth, and being anticarcinogenic (Stojanovic et al. Arch Biochem Biophy 2001, 391:79–89). By suppressing the induction of phosphorylation and nuclear translocation of p65 subunit by tumor necrosis factor-alpha (TNF-α), resveratrol blocked the activation of NF-κB (Manna et al. J. Immunol. 2000, 164:6509–19). Since activation of NF-κB by radiation therapy or chemotherapy in cancer patients leads to mucositis, compounds that inhibit the activation or action of NF-κB may be effective in treating or preventing mucositis.

Accordingly, the invention features a method for the treatment or prevention of mucositis. This method is based on the administration of a therapeutically effective amount of an inhibitor of NF-κB to a patient undergoing or about to undergo radiation or chemotherapy treatments for cancer.

Since resveratol has shown efficacy in treating mucositis, other hydroxystilbenes, e.g., the compounds of formula I, may show similar or greater efficacy.

Additional compounds that are known to inhibit NF-κB include, without limitation, α-lipoic acid (Sen et al., 1998; Suzuki et al., 1992), α-tocopherol (Islam et al., 1998), Anetholdithiolthione (ADT) (Sen et al., 1996), Butylated hydroxyanisole (BHA) (Israel et al., 1992; Schulze-Osthoff et al., 1993), Cepharanthine (Okamoto et al., 1994), Caffeic Acid Phenethyl Ester (3,4-dihydroxycinnamic acid, CAPE) (Natarajan et al., 1996), Catechol Derivatives (Suzuki et al., 1994), Diethyldithiocarbamate (DDC) (Schreck et al., 1992b), Deferoxamine (Sappey et al., 1995), Dihydrolipoic Acid (Suzuki et al., 1995), Disulfiram (Schreck et al., 1992b), Dimethyldithiocarbamates (DMDTC) (Pyatt et al., 1998a), Curcumin (Diferulolylmethane) (Singh and Aggarwal, 1995b), Ebselen (Schreck et al., 1992b), EPC-K1 (phosphodiester compound of vitamin E and vitamin C) (Hirano et al., 1998) Epigallocatechin-3-gallate (EGCG; green tea polyphenols) (Lin et al., 1997; Yang et al.,1998), Ethylene Glycol Tetraacetic Acid (EGTA) (Janssen et al., 1999), Gamma-glutamylcysteine synthetase (gamma-GCS) (Manna et al., 1999), Glutathione (Cho et al., 1998; Schreck et al., 1992b), L-cysteine (Mihm et al., 1991) Lacidipine (Cominacini et al., 1998), Manganese Superoxide Dismutase (Mn-SOD) (Manna et al., 1998), Melatonin (Gilad et al., 1998; Mohan et al., 1995), N-acetyl-L-cysteine (NAC) (Schreck et al., 1991), Nordihydroguaiaritic acid (NDGA) (Brennan et al., 1998; Israël et al.,1992; Schulze-Osthoff et al., 1993; Staal et al., 1993), Orthophenanthroline (Schreck et al., 1992b), Phenylarsine oxide (PAO, tyrosine phosphatase inhibitor) (Arbault et al., 1997), Pyrrolidinedithiocarbamate (PDTC) (Schreck et al., 1992a), Quercetin (Musonda and Chipman, 1998), Rotenone (Schulze-Osthoff et al., 1993), S-allyl-cysteine (SAC, garlic compound) (Geng et al., 1997), Tepoxalin (5-(4-chlorophenyl)-N- hydroxy-(4-methoxyphenyl) -N-methyl-1H -pyrazole-3-propanamide) (Kazmi et al., 1995), Vitamin C (Staal et al., 1993), Vitamin E derivatives (Suzuki and Packer, 1993a), α-torphryl succinate (Staal et al., 1993; Suzuki and Packer, 1993b), α-torphryl acetate (Suzuki et al., 1993a), PMC (2,2,5,7,8-pentamethyl-6-hydroxychromane) (Suzuki et al., 1993a), Peptide Aldehydes: ALLnL (N-acetyl-leucinyl-leucinyl-norleucinal, MG101), LLM (N-acetyl-leucinyl-leucinyl-methional), Z-LLnV (carbobenzoxy-leucinyl-leucinyl-leucinal, MG132) (Palombella et al., 1994; Grisham et al., 1999; Jobin et al., 1998a), Lactacystin, β-lactone (Fenteany et al., 1998; Grisham et al., 1999), Boronic Acid Peptide (Grisham et al., 1999; Iqbal et al., 1995), Ubiquitin Ligase Inhibitors (Yaaron et al., 1997), Cyclosporin A (Frantz et al., 1994; Marienfield et al., 1997; McCaffrey et al. 1994; Meyer et al., 1997; Wechsler et al., 1994), FK506 (Tacrolimus) (Okamoto et al., 1994; Venkataraman et al., 1995), Deoxyspergualin (Tepper et al., 1995), APNE (N-acetyl-DL-phenylalanine-β-naphthylester) (Higuchi et al., 1995), BTEE (N-benzoyl L-tyrosine-ethylester) (Rossi et al., 1998), DCIC (3,4-dichloroisocoumarin), DFP (diisopropyl fluorophosphate), TPCK (N-α-tosyl-L-phenylalanine chloromethyl ketone), TLCK (N-α-tosyl-L-lysine chloromethyl ketone) (D'Acquisto et al., 1998), Aspirin, sodium salicylate (Frantz and O'Neill, 1995; Kopp and Ghosh, 1994; Yin et al., 1998), BAY-117821 (E3((4-methylphenyl)-sulfonyl)-2-propenenitrile), BAY-117083 (E3((4-t-butylphenyl)-sulfonyl)-2-propenenitrile), Cycloepoxydon, 1-Hydroxy-2-hydroxymethyl-3-pent-1-enylbenzene (Gehrt et al., 1998), Extensively oxidized low density lipoprotein (ox-LDL), 4-Hydroxynonenal (HNE) (Brand et al., 1997; Page et al., 1999), Ibuprofen (Palayoor et al., 1999), Nitric Oxide (NO) (Katsuyama et al., 1998; Matthews et al., 1996), Prostaglandin A1 (Rossi et al., 2000), Sanguinarine (pseudochelerythrine, 13-methyl-[1,3]-benzodioxolo-[5,6-c]-1,3-dioxolo-4,5 phenanthridinium) (Chaturvedi et al., 1997), Sulfasalazine (Wahl et al., 1998), Sulindac (Yamamato et al., 1999), YopJ (encoded by *Yersinia pseudotuberculosis*) (Schesser et al., 1998), α-melanocyte-stimulating hormone (α-MSH) (Manna and Aggarwal, 1998a), β-lapachone (Manna et al., 1999a), Capsaicin (8-methyl-N-vanillyl-6-nonenamide) (Singh et al., 1996b), Core Protein of Hepatitis C virus (HCV) (Shrivastava et al., 1998), Diamide (tyrosine phosphatase inhibitor) (Toledano and Leonard, 1991; Singh and Aggarwal, 1995a), Emodin (3-methyl-1,6,8-trihydroxyanthraquinone) (Kumar et al., 1998), Erbstatin (tyrosine kinase inhibitor) (Natarajan et al., 1998), Estrogen (E2) (Sun et al., 1998), Fungal gliotoxin (Pahl et al., 1996), Genistein (tyrosine kinase inhibitor) (Natarajan et al., 1998), IL-13 (Manna and Aggarwal, 1998b), Leflunomide metabolite (A77 1726) (Manna and Aggarwal, 1999), Pervanadate (tyrosine phosphatase inhibitor) (Singh and Aggarwal, 1995a; Singh et al., 1996a), Phenylarsine oxide (PAO, tyrosine phosphatase inhibitor) (Mahboubi et al., 1998, Singh and Aggarwal, 1995a), Resiniferatoxin (Singh et al., 1996), Sesquiterpene lactones (parthenoide) (Hehner et al., 1998), β-amyloid protein (Bales et al., 1998), Glucocorticoids (dexametasone, prednisone, methylprednisolone) (Auphan et al., 1995; Brostjan et al., 1996; Ray and Prefontaine, 1994; Scheinman et al., 1995), IL-10 (Ehrlich et al., 1998; Lentsch et al., 1997), IL-11 (Trepicchio and Dorner, 1998), Leptomycin B (LMB) (Rodriguez et al., 1999), NLS Cell permeable peptides (Lin et al., 1995), o,o'-bismyristoyl thiamine disulfide (BMT) (Shoji et al., 1998), ADP ribosylation inhibitors (nicotinamide, 3-aminobenzamide) (Le Page et al., 1998), Atrial Natriuretic Peptide (ANP) (Gerbes et al., 1998), Atrovastat (HMG-CoA reductase inhibitor) (Bustos et al., 1998; Hemandez-Presa et al., 1998), Calcitriol (1a,25-dihydroxyvitamine D3) (Harant et al., 1998), Clarithromycin (Miyanohara et al., 2000), Diamide (Toledano and Leonard, 1991), E3330 (quinone derivative) (Hiramoto et al., 1998), Glycyrrhizin (Wang et al., 1998), Herbimycin A (Iwasaki et al., 1992; Mahon and O'Neill,1995), Hypericin (Bork et al., 1999), Hydroquinone (HQ) ( Pyatt et al., 1998b), IL-4 (Manna and Aggarwal 1999), IkB-like proteins (encoded by ASFV) (Powell et al., 1996; Revilla et al., 1998), KT-90 (morphine synthetic derivative) (Sueoka et al., 1998), Metals (chromium, cadmium, gold, mercury, zinc, arsenic) (Shumilla et al., 1998; Yang et al., 1995), Mevinolin, 5'-methylthioadenosine (MTA) (Law et al., 1992), N-ethyl-maleimide (NEM) (Toledano and Leonard, 1991), Nicotine (Sugano et al., 1998), Pentoxifylline (1-(5'-oxohexyl) 3,7-dimetylxanthine, PTX) (Biswas et al., 1993; Wang et al., 1997), Phenyl-N-tert-butylnitrone (PBN) (Kotake et al., 1998), Pituitary adenylate cyclase-activating polypeptide (PACAP) (Delgado et al., 1998), Pyrithione ( Kim et al., 1999), Quinadril (ACE inhibitor) (Bustos et al., 1998; Hernandez-Presa et al., 1998), Ribavirin (Fiedler et al., 1996), Secretory leukocyte protease inhibitor (SLPI) (Jin et al., 1997), Serotonin derivatives (N-(p-coumaroyl) serotonin, SC) (Kawashima et al., 1998), Silymarin (Saliou et al., 1998), Vascular endothelial growth factor (VEGF) (Oyama et al., 1998; Gabrilovich et al., 1998), Vasoactive intestinal peptide (VIP) (Delgado et al., 1998), D609 (phosphatidylcholine-phospholipase C inhibitor) (Bergmann et al., 1998), RO31-8220 (PKC inhibitor) (Bergmann et al., 1998), SB203580 (p38 MAPK inhibitor) (Bergmann et al., 1998), Triptolide (PG490, extract of Chinese herb) (Qiu et al., 1999), LY294,002 (Sizemore et al., 1999), Mesalamine (Egan et al., 1999), Wortmannin (fungal metabolite) (Manna and Aggarwal, 2000), lactacystin, idoxifene, raloxifene, droloxifene, tiremifene, and tamoxifen. Further examples of compounds that inhibit NF-κB are disclosed in Narayanan et al. (U.S. Pat. No. 5,591,840), Bennett et al. (U.S. Pat. No. 6,069,008), Lai et al. (U.S. Pat. No. 6,316,502), Morishita et al. (U.S. Pat. No. 6,262,033), Qabar et al. (U.S. Pat. No. 6,117,896), and Iino et al. (U.S. Pub. No. 2001/018441), each of which is hereby incorporated by reference.

Flavinoids, e.g., those found in soybean (such as genestein), can also be used to attenuate mucositis according to the invention. Among other possible flavinoids that can be used in the invention are galloyl flavonol glycosides such as quercetin or kaempferol.

Topical application is preferred, but compounds can be administered using any standard means for administering therapeutic compounds, including, without limitation, oral, sublingual, intravenous, and intraperitoneal injection. Dosages and timing of administration can be determined using routine methods for such determination, e.g. a therapeutically effective amount is administered one, two, or three times a day. The compounds may be administered, for example, at any time before, during, or after radiation or chemotherapy. Treatment may be continued as long as necessary.

EXAMPLE 1

Animal Model of Treatment of Mucositis with Resveratrol.

Hamster models of chemotherapy-induced mucositis and radiation-induced mucositis have been developed. In the latter model, specific doses of acute radiation were targeted to the designated mucosa, with protection of other areas by a customized lead shield. The reproducibility of the model has been validated, with the consistent appearance of ulcerative mucositis between days 15 and 18 following radiation. Using this model, the efficacies of various topical agents have been tested for their abilities to modify the course of radiation-induced mucositis.

Project Rationale and Protocol

Study Parameters. This study analyzed resveratrol in both topical and intraperitoneal dosing at concentrations of 1 mM and 5 mM. The control group was dosed topically with water.

Induction of mucositis by an irradiation regimen. An acute radiation dose of 40 Gy on day 0 was administered in order to produce severe mucositis around day 15. The use of acute radiation to induce mucositis was preferable to the use of either fractionated radiation or chemotherapy for these initial studies. The acute model had little systemic toxicity, resulting in fewer animal deaths. This fact permitted the use of smaller groups in the initial studies. The acute model has been used successfully to demonstrate the presence or absence of efficacy for a large number of compounds. The acute radiation model is therefore appropriate as an initial protocol for screening diverse families of compounds.

Mucositis Evaluation

The grade of mucositis was scored, starting from day 6 following irradiation (which occurs on day 0), and for every second day thereafter, through and including day 20. The effect on mucositis of each drug treatment compared to placebo was assessed according to the following parameters:

The difference in the number of days hamsters in each group have severe (score $\geq 3$) mucositis. On each Evaluation Day, the number of animals with a blinded mucositis score of >2 in each drug treatment group, was compared to the control group. Differences were analyzed on a daily as well as a cumulative basis. Successful treatment was considered a statistically significant lower number of hamsters with a score $\geq 3$ in a drug treatment group, versus control as determined by chi-square analysis.

The rank sum differences in daily mucositis scores. For each day of evaluation, the scores of the control group were compared to those of the treated group using the non-parametric rank sum analysis. Treatment success was considered as a statistically significant lowering of scores in the treated group on 2 or more days from day 8 to day 20.

Animals

Male Golden Syrian hamsters (Charles River Laboratories, Wilmington, Mass. or Harlan Sprague Dawley, Indianapolis, Ind.), aged 5 to 6 weeks, with body weight approximately 90 g at project commencement, were used. Animals were individually numbered using an ear punch and housed in small groups of approximately 6 animals per cage. Animals were acclimatized for at least one week prior to project commencement. During this period, the animals were observed daily in order to reject animals that presented poor condition.

Animal Randomization and Allocations.

This study used forty (40) hamsters that were randomly divided into five groups of eight animals per group. Each group was assigned a different treatment as follows:

| Group 1 | Animals 1–8 | topical, tid | water |
| Group 2 | Animals 9–16 | intraperitoneal, qd | 1 mM Resveratrol |
| Group 3 | Animals 17–24 | intraperitoneal, qd | 5 mM Resveratrol |
| Group 4 | Animals 25–32 | topical, tid | 1 mM Resveratrol |
| Group 5 | Animals 33–40 | topical, tid | 5 mM Resveratrol |

Mucositis Induction

Mucositis was induced using an acute radiation protocol. A single dose of radiation (40 Gy/dose) was administered to all animals on Day 0. Radiation was generated with a 250 kilovolt potential (15 mA) source at a focal distance of 50 cm, hardened with a 0.35 mm Cu filtration system. Irradiation targeted the left buccal pouch mucosa at a rate of 121.5 cGy/minute. Prior to irradiation, animals were anesthetized with an intraperitoneal injection of sodium pentobarbital (80 mg/kg). The left buccal pouch was everted, fixed, and isolated using a lead shield.

Dosing and Drug Application

The test compounds were kept frozen and protected from light when not in use during the entire study. Each day of dosing, an aliquot of test compound was removed from the plastic bottles using a sterile syringe, and 0.2 ml of the compound was injected into each animal in groups 2 and 3. Intraperitoneal (IP) dosing was performed once per day from day −1 to day 20.

Topical dosing was performed 3 times per day for animals in groups 1, 4 and 5. A needleless tuberculin syringe, containing 0.2 ml of the test compound or water, was inserted into the left cheek pouch and the drug deposited into the pouch.

All hamsters were weighed daily and their survival recorded, in order to assess possible differences in animal weight among treatment groups as an indication for mucositis severity and/or possible toxicity resulting from the treatments.

Mucositis Evaluation

Starting on Day 6 of each study and then every second day thereafter (Days 8, 10, 12, 14, 16, 18, and 20), animals were photographed and evaluated for mucositis. Parameters to be measured include the mucositis score, weight change, and survival. For the evaluation of mucositis, the animals were anesthetized with inhalation anesthetics, and the left pouch everted. Mucositis was scored visually by comparison to a validated photographic scale, ranging from 0 for normal, to 5 for severe ulceration (clinical scoring). In descriptive terms, this scale was defined as follows:

| Score: | Description: |
|---|---|
| 0 | Pouch completely healthy. No erythema or vasodilation |
| 1 | Light to severe erythema and vasodilation. No erosion of mucosa |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth) |

A score of 1–2 was considered to represent a mild stage of the disease, whereas a score of 3–5 was considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring).

Assessment of Results

Statistical differences between treatment groups were determined using Student's t-test, Mann-Whitney U test and chi-square analysis with a critical value of 0.05.

Results

Figure 1:
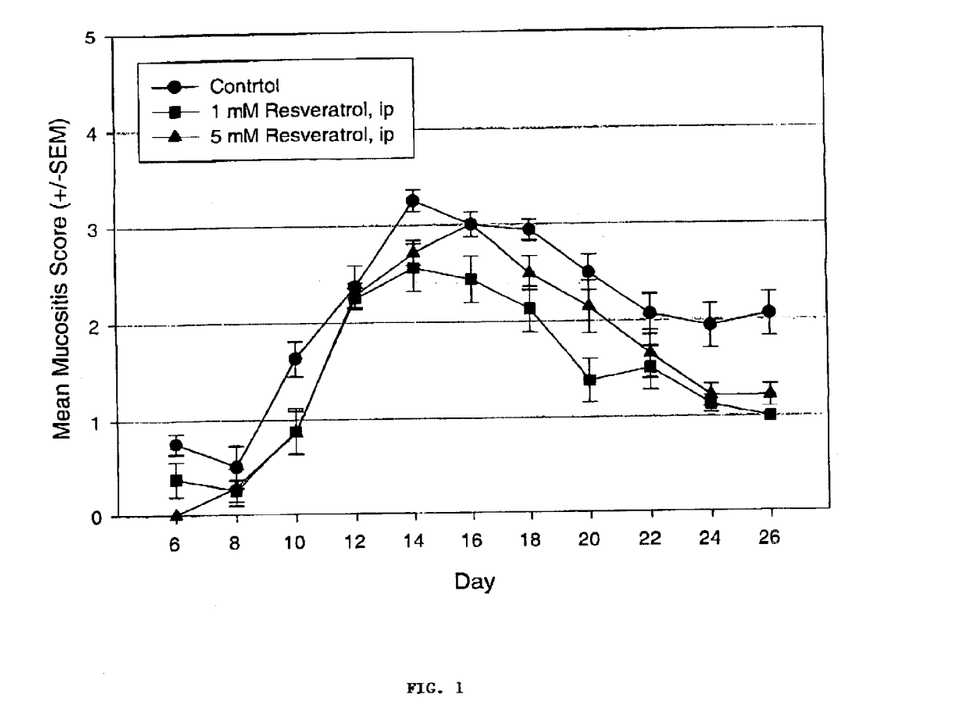
FIG. 1 is a graph of the mean mucositis scores of control hamsters and hamsters treated with 1 mM and 5 mM of resveratrol as a function of days after exposure to radiation.
Figure 2:
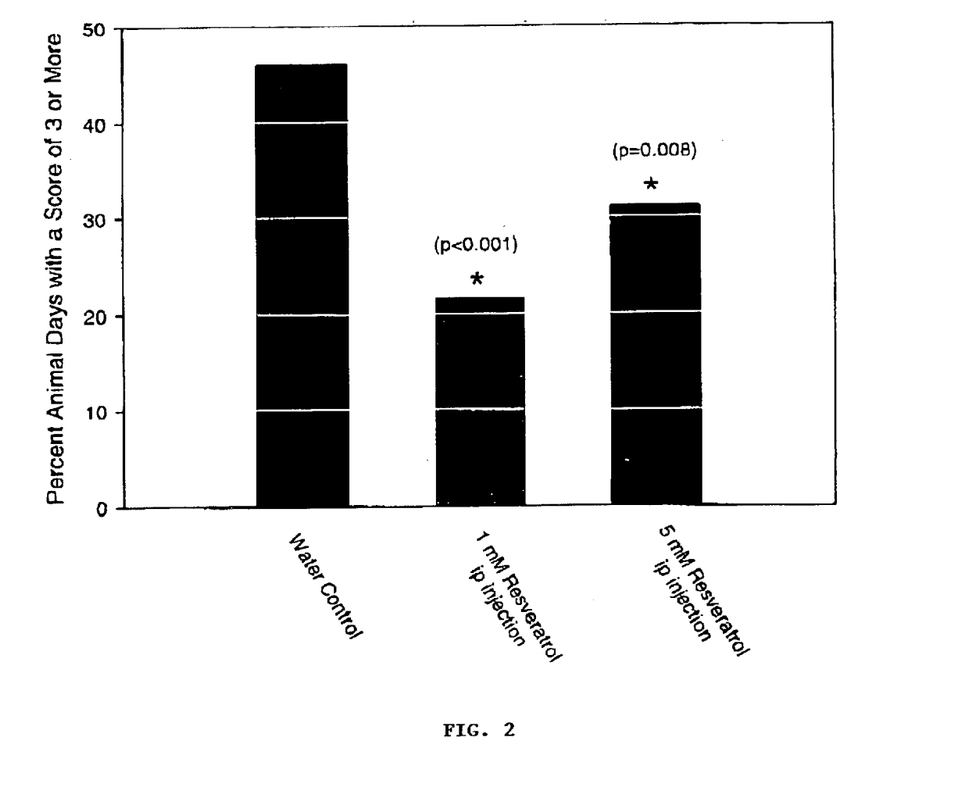
FIG. 2 is a bar graph showing the number of days, as a percentage, that control hamsters and hamsters treated with 1 mM and 5 mM of resveratrol had a mucositis score of 3 or more.
Figure 3:
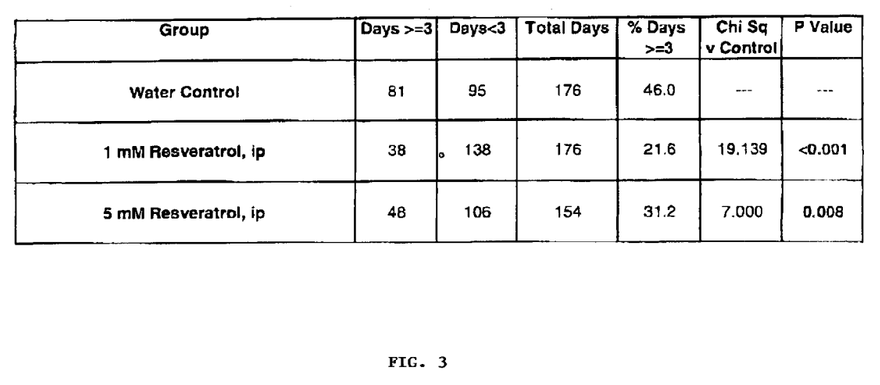
FIG. 3 is a table listing statistical data for comparison between control hamsters and hamsters treated with 1 mM and 5 mM of resveratrol.
Figure 4:
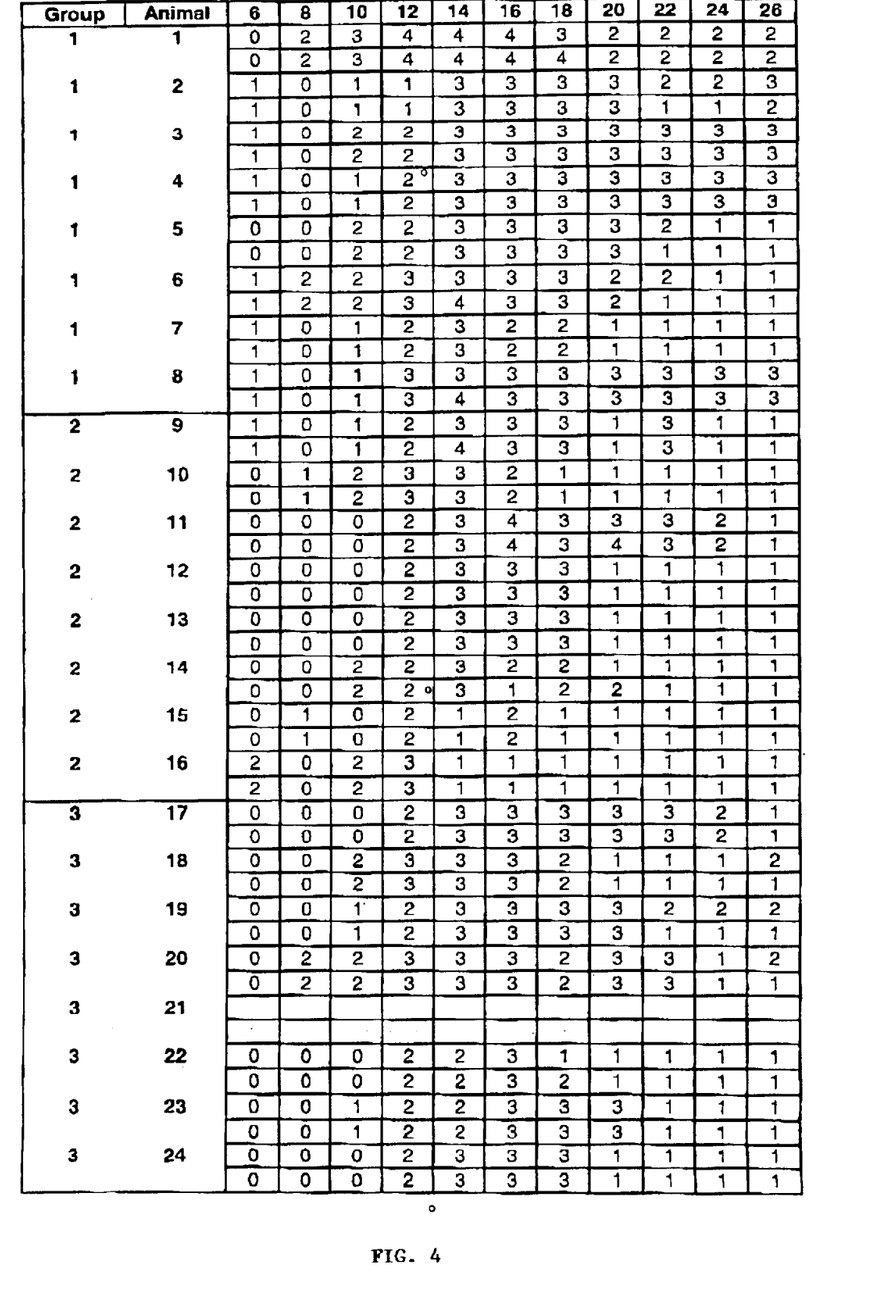
FIG. 4 is a table listing the mucositis scores for control hamsters and hamsters treated with 1 mM and 5 mM resveratrol.

The results of the control and IP experiments are shown in FIGS. 1–4. The data in FIG. 1 show the mean mucositis score as a function of days after exposure to radiation for control hamster and hamsters treated with 1 mM and 5 mM of resveratrol (IP administration). As illustrated in FIG. 2., treatment with resveratrol reduced the severity of mucositis compared to the control. Treatment with 1 mM resveratrol was more effective than treatment with 5 mM of resveratrol. The percentage of days where hamsters had a mucositis score of less than three was reduced from 46.0% for the control to 31.2% for treatment with 5 mM and to 21.6% for treatment with 1 mM of resveratrol (FIG. 3). FIG. 4 lists the individual scores for each hamster in groups 1–3, as defined above, as a function of time.

The results of the experiments on topical application of resveratrol, although not statistically significant, indicated a trend of efficacy.

EXAMPLE 2

Synthesis of Hydroxystilbene Derivatives.

Compounds of formula I above can be synthesized by methods known in the art, for example, by the methods of Moreno-Manas et al. Anal. Quim. 1985, 81:157–161; Jeandet et al. Am. J. Enol. Vitic. 1991, 42:41–46; Goldberg et al. Anal. Chem. 1994, 66:3959–3963; and March *Advanced Organic Chemistry*, 4$^{th}$ ed., Wiley: N.Y., 1992.

Other Embodiments

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the art, are intended to be within the scope of the invention.

All publications, patents, and patent applications mentioned in this specification are hereby incorporated by reference to the same extent as if each individual publication, patent, or patent application was specifically and individually to be incorporated by reference.

Other embodiments are within the claims.

References

1. Sen C K, Tirosh O, Roy S, Kobayashi M S and Packer L (1998) A positively charged a-lipoic acid analogue with increased cellular uptake and more potent immunomodulatory activity. Biochemical and Biophysical Research Communications 247 223–228.
2. Suzuki Y J, Aggarwal B B and Packer L (1992) a-lipoic acid is a potent inhibitor of NF-kB activation in human T cells. Biochemical and Biophysical Research Communications 189 1709–1715.
3. Islam K N, Devaraj S and Kialal I (1998) a-tocopherol enrichment of monocytes decreases agonist-induced adhesion to human endothelial cells. Circulation 98 2255–2261.
4. Sen C K, Traber K and Packer L (1996) Inhibition of NF-kB activation in human T-cell lines by anetholdithiolthione. Biochemical and Biophysical Research Communications 218 148–153.
5. Israël N, Gougerot-Pocidalo M A, Aillet F and Virelizier J L (1992) Redox status of cells influences constitutive or induced NF-kB translocation and HIV long terminal repeat activity in human T and monocytic cell lines. Journal of Immunology 149 3386–3393.
6. Schulze-Osthoff K, Beyaert R, Vandvoorde V, Haegeman G and Fiers W (1993) Nordihydroguaiaretic acid inhibition of NF-kB. EMBO Journal 12 3095–3104.
7. Okamoto S-I, Mukaida N, Yasumoto K, Rice N, Ishikawa Y, Horiguchi H, Murakami S and Matsushima K (1994) The interleukin-8 AP-1 and kB-like sites are genetic end targets of FK506-sensitive pathway accompanied by calcium mobilization. Journal of Biological Chemistry 269 8582–8589.
8. Natarajan K, Singh S, Burke Jr T R, Grunberger D and Aggarwal B B (1996) Caffeic acid phenethyl ester is a potent and specific inhibitor of activation of nuclear transcription factor NF-kB. Proceedings of the National Academy of Sciences USA 93 9090–9095.
9. Suzuki Y J and Packer L (1994) Inhibition of NF-kB transcription factor by catechol derivatives. Biochemistry and Molecular Biology International 32 299–305.
10. Schreck R, Meier B, Männel D N, Droge W and Baeuerle P A (1992b) Dithiocarbamates as potent inhibitors of nuclear factor kB activation in intact cells. Journal of Experimental Medicine 175 1181–1194.
11. Sappey C, Boelaert J R, Legrand-Poels S, Forceille C, Favier A, Piette J. (1995) Iron chelation decreases NF-kappa B and HIV type 1 activation due to oxidative stress.
12. Suzuki Y J, Mizuno M, Tritschler H J and Packer L (1995) Redox regulation of NF-kB DNA binding activity by dihydrolipoate. Biochemical and Molecular Biology International 36 241–246.
13. Pyatt D W, Gruntmeir J, Stillman W S, Irons R D. (1998) Dimethyldithiocarbamate inhibits in vitro activation of primary human CD4+ T lymphocytes. Toxicology. 128 83–90.
14. Singh S and Aggarwal B B (1995b) Activation of transcription factor NF-kB is suppressed by curcumin (diferulolylmethane). Journal of Biological Chemistry 270 24995–25000.
15. Hirano F, Tanaka H, Miura T, Hirano Y, Okamoto K, Makino Y and Makino I (1998) Inhibition of NF-kB-dependent transcription of human immunodeficiency virus 1 promoter by a phosphodiester compound of vitamin C and vitamin E, EPC-K1. Immunopharmacology 39 31–38.
16. Lin Y L and Lin J K (1997) (−)-epigallocatechin-3-gallate blocks the induction of nitric oxide synthase by down-regulating lipopolysaccharide-induced activity of transcription factor nuclear factor-kB. Molecular Pharmacology 52 465–472.
17. Yang F, de Villiers W J S, McClain C J and Varilek G W (1998) Green tea polyphenols block endotoxin-induced tumor necrosis factor-production and lethality in a murine model. Journal of Nutrition 128 2334–2340.
18. Janssen Y M, Sen C K (1999) NF-kB activity in response to oxidants and antioxidants. Methods in Enzymology 300 363–74.
19. Manna S K, Kuo M T and Aggarwal B B (1999b) Overexpression of gamma-glutamylcysteine synthetase suppresses tumor necrosis factor-induced apoptosis and activation of nuclear transcription factor-kappa B and activator protein-1. Oncogene 18 4371–4382.
20. Cho S, Urata Y, Iida T, Goto S, Yamaguchi M, Sumikawa K and Kondo T (1998) Glutathione downregulates the phosphorylation of IkB: autoloop regulation of the NF-kB-mediated expression of NF-kB subunits by TNF-a in mouse vascular endothelial cells. Biochemical and Biophysical Research Communications 253 104-108.

21. Mihm S, Ennen J, Pessara U, Kurth R and Dröge W (1991) Inhibition of HIV-1 replication and NF-kB activity by cysteine and cysteine derivatives. AIDS 5 497–503.
22. Cominacini L, Garbin U, Pasini A F, Davoli A, Campagnola M, Pastorino A M, Gaviraghi G, and Lo Cascio V (1998) Oxidized low-density lipoprotein increases the production of intracellular reactive oxygen species in endothelial cells: inhibitory effect of lacidipine. Journal of Hypertension 16 1913–1919.
23. Manna S K, Zhang H J, Yan T, Oberly L W and Aggarwal B B (1998) Overexpression of manganese superoxide dismutase suppresses tumor necrosis factor-induced apoptosis and activation of nuclear transcription factor-kB and activator protein-1. Journal of Biological Chemistry 273 13245–13254.
24. Gilad E, Wong H R, Zingarelli B, Virag L, O'Connor M, Salzman A L and Szabo C (1998) Melatonin inhibits expression of the inducible isoform of nitric oxide synthase in murine macrophages: role of inhibition of NF-kB activation. FASEB Journal 12 685–693.
25. Mohan N, Sadeghi K, Reiter R J, Meltz M L. (1995) The neurohormone melatonin inhibits cytokine, mitogen and ionizing radiation induced NF-kappa B. Biochem Mol Biol Int. 37 1063–70.
26. Schreck R, Rieber P and Baeuerle P A (1991) Reactive oxygen intermediates as apparently widely used messengers in the activation of the NF-kB transcription factor and HIV-1. EMBO Journal 10 2247–2258.
27. Brennan P and O'Neill L A (1998) Inhibition of nuclear factor kB by direct modification in whole cells--mechanism of action of nordihydroguaiartic acid curcumin and thiol modifiers. Biochemical Pharmacology 55 965–973.
28. Schulze-Osthoff K, Beyaert R, Vandvoorde V, Haegeman G and Fiers W (1993) Nordihydroguaiaretic acid inhibition of NF-kB. EMBO Journal 12 3095–3104.
29. Staal F J T, Roederer M, Raju P A, Anderson M T Ela S W, Herzenberg L A and Herzenberg L A (1993) Antioxidants inhibit stimulation of HIV transcription. AIDS Research and Human Retroviruses 9 299–305.
30. Arbault S, Edeas M, Legrand-Poels S, Sojic N, Amatore C, Piette J, Best-Belpomme M, Lindenbaum A and Vuillaume M (1997) Phenylarsine oxide inhibits ex vivo HIV-1 expression. Biomedical Pharmacotherapy 51 430–438.
31. Schreck R, Meier B, Männel D N, Dröge W and Baeuerle P A (1992a) Dithiocarbamates as potent inhibitors of nuclear factor kB activation in intact cells. Journal of Experimental Medicine 175 1181–1194.
32. Musonada C A and Chipman J K (1998) Quercetin inhibits hydrogen peroxide ($H_2O_2$)-induced NF-kB DNA binding activity and DNA damage in HepG2 cells. Carcinogenesis 19 1583–1589.
33. Geng Z, Rong Y, Lau B H (1997) S-allyl cysteine inhibits activation of NF-κβ in human T cells. Free Radical Biology and Medicine 23 345–50.
34. Kazmi S, Plante R, Visconte V, taylor G, Zhou L and Lau C (1995) Suppression of NF-kB dependent gene expression by tepoxalin, a dual inhibitor of cyclooxygenase and 5-lipoxygenase. Journal of Cellular Biochemistry 57 299–310.
35. Suzuki Y J and Packer L (1993a) Inhibition of NF-kB activation by vitamin E derivatives. Biochemical and Biophysical Research Communications 193 277–283.
36. Suzuki Y J and Packer L (1993b) Inhibition of NF-kB DNA-binding by activaty by a-tocpheryl succinate. Biochemistry and Molecular Biology International 31 693–700.
37. Palombella V J, Rando O J, Goldberg A L and Maniatis T (1994) The ubiquitin-proteasome pathway is required for processing the NF-kB1 precursor protein and the activation of NF-kB. Cell 78 773–785.
38. Grisham M B, Palombella V J, Elliott P J, Conner E M, Brand S, Wong H L, Pein C, Mazzola L M, Destree A, Parent L, Adams J (1999) inhibition of NF-κβ activation in vitro and in vivo: role of 26S proteasome. Methods in Enzymology 300 345–63.
39. Jobin C, Hellerbrand C, Licato L L, Brenner D A and Sartor R B (1998) Mediatioin by NF-kB cytokine induced expression by intercellular adhesion molecule 1 (ICAM-1) in an intestinal epithelial cell line, a process blocked by proteasome inhibitors. Gut 42 779–787.
40. Fenteany G, Schreiber S L. (1998) Lactacystin, proteasome function, and cell fate. J Biol Chem. 273 8545–8.
41. Iqbal M, Chatterjee S, Kauer J C, Das M, Messina P, Freed B, Biazzo W, Siman R. (1995) Potent inhibitors of proteasome. J Med Chem. 38 2276–7.
42. Yaron A, Gonen H, Alkalay I, Hatzubai A, Jung S Beyth S, Mercurio F, Manning A M, Ciechanover A, Ben-Neriah Y (1997) Inhibition of NF-κβ cellular function via specific targeting of the I-κβ-ubiquitin ligase. EMBO journal 16 6486–94.
43. Frantz B, Nordby E C, Bren G, Steffan N, Paya C V, Kincaid R L, Tocci M J, O'Keefe S J and O'Neill E A (1994) Calcineurin acts in synergy with PMA to inactivate IkB, an inhibitor or NF-kB. EMBO Journal 13 861–870.
44. Marienfeld R, Neumann M, Chuvpilo S, Escher C, Kneitz B, Avots A, Schimpl A and Serfling E (1997) Cyclosporin A interferes with the inducible degradation of NF-kB inhibitors, but not with the processing of p105/NF-kB1 in T cells. European Journal of Immunology 27 1601–1609.
45. McCaffrey P G, Kim P K, Valge-Archer V E, Sen R and Rao A (1994) Cyclosporin A sensitivity of the NF-kB site of the IL2Ra promoter in untransformed murine T cells. Nucleic Acids Research 22 2134–2142.
46. Meyer S, Kohler N G and Joly A (1997) Cyclosporine A is an uncompetitive inhibitor of proteasome activity and prevents NF-kB activation. FEBS Letters 413 354–358.
47. Wechsler A S, Gordon M C, Dendorfer U and LeClair K (1994) Induction of IL-8 expression in T cells uses the CD28 costimulatory pathway. Journal of Immunology 153 2515–2523.
48. Okamoto S-I, Mukaida N, Yasumoto K, Rice N, Ishikawa Y, Horiguchi H, Murakami S and Matsushima K (1994) The interleukin-8 AP-1 and kB-like sites are genetic end targets of FK506-sensitive pathway accompanied by calcium mobilization. Journal of Biological Chemistry 269 8582–8589.
49. Venkataraman L, Burakoff S J and Sen R (1995) FK506 inhibits antigen receptor-mediated induction of c-rel in B and T lymphoid cells. Journal of Experimental Medicine 181 1091–1099.
50. Tepper M A, Nadler S G, Esselstyn J M, Sterbenz K G. (1995) Deoxyspergualin inhibits kappa light chain expression in 70Z/3 pre-B cells by blocking lipopolysaccharide-induced NF-kappa B activation. J Immunol. 155 2427–36.
51. Higuchi M, Singh S, Chan H, Aggarwal B B. (1995) Protease inhibitors differentially regulate tumor necrosis factor-induced apoptosis, nuclear factor-kappa B activation, cytotoxicity, and differentiation. Blood. 1995 86 2248–56.
52. Rossi A, Elia G and Santoro M G (1998) Activation of the heat shock factor 1 by serine protease inhibitors. An effect associated with nuclear factor-kB inhibition. Journal of Biological Chemistry 273 16446–16452.
53. D'Acquisto F, Sautebin L, Iuvone T, Di Rosa M and Carnuccio R (1998) Prostaglandins prevent inducible nitric oxide synthase protein expression by inhibiting nuclear factor kB activation in J774 macrophages. FEBS Letters 440 76–80.
54. Frantz B and O'Neill E A (1995) The effect of sodium salicylate and on NF-kB. Science 270 2017–2018.and Response by Ghosh S and Kopp E (1995) Science 270 2018–2019.
55. Kopp E and Ghosh S (1994) Inhibition of NF-kB by sodium salicylate and aspirin. Science 265 956–959.
56. Yin M-J, Yamamoto Y and Gaynor R B (1998) The anti-inflammatory agents aspirin and salicylate inhibit the activity of IkB kinase-b. Nature 396 77–80.
57. Gehrt A, Erkel G, Anke T and Sterner O (1998) Cycloepoxydon, 1-hydroxy-2-hydroxymethyl-3-pent-1-enylbenzene and 1-hydroxy-2-hydroxy3-pent-1,3-dienylbenzene, new inhibitors of eukaryotic signal transduction. Journal of Antibiotics 51 455–463.
58. Brand K, Eisele T, Kreusel U, Page M, Page S, Haas M, Gerling A, Kaltschmidt C, Neumann F J, Mackman N, Baeurele P A, Walli A K, Neumeier D. (1997) Dysregulation of monocytic nuclear factor-kappa B by oxidized low-density lipoprotein. Arterioscler Thromb Vasc Biol. 17 1901 –9.
59. Page S, Fischer C, Baumgartner B, Haas M, Kreusel U, Loidl G, Hayn M, Ziegler-Heitbrock H W, Neumeier D and Brand K (1999) 4-Hydroxynonenal prevents NF-kappaB activation and tumor necrosis factor expression by inhibiting IkappaB phosphorylation and subsequent proteolysis. J Biol Chem 274 11611–11618.
60. Palayoor S T, Youmell M Y, Calderwood S K, Coleman C N, Price B D. (1999) Constitutive activation of IkappaB kinase alpha and NF-kappaB in prostate cancer cells is inhibited by ibuprofen. Oncogene. 18 7389–94.
61. Katsuyama K, Shichiri M, Marumo F and Hirata Y (1998) Role of nuclear factor-kB activation in cytokine- and sphingomyelinase-stimulated inducible nitric oxide synthase gene expression in vascular smooth muscle cells. Endocrinology 139 4506–4512.
62. Matthews J R, Botting C H, Pacino M, Morris H R and Hay R T (1996) Inhibition of NF-kB DNA binding by nitric oxide. Nucleic Acids Research 24 2236–2242.
63. Rossi A, Kapahi P, Matoli G, Takahashi T, Chen Y, Karin M and Santoro MG (2000) Anti-inflammatory cyclopentenone prostaglandins are direct inhibitors of IkB kinase. Nature 403 103–108.
64. Chaturvedi M M, Kumar A, Darnay B G, Chainy G B N, Aggarwal S and Aggarwal B B (1997) Sanguinarine (pseudochelerythrine) is a potent inhibitor of NF-kB activation, IkBa phosphorylation and degradation. Jounral of Biological Chemistry 272 30129–30134.
65. Wahl C, Liptay S, Adler G, Schmid R M. (1998) Sulfasalazine: a potent and specific inhibitor of nuclear factor kappa B. J Clin Invest. 101 1163–74.
66. Yamamoto Y, Yin M-J, Lin K-M and Gaynor R (1999) Sulindac inhibits activation of the NF-kB pathway. Journal of Biological Chemistry 274 27307–27314.
67. Schesser K, Spiik A K, Dukuzumuremyi J M, Neurath M F, Pettersson S and Wolf-Watz H (1998) The yopJ locus is required for Yersinia-mediated inhibition of NF-kB activation and cytokine expression: YOPJ contains a eukaryotic SH2-like domain that is essential for its repressive activity. Molecular Microbiology 28 1067–1079.
68. Manna S K and Aggarwal B B (1998a) a-melanocyte-stimulating hormone inhibits the nuclear transcription factor NF-kB activation induced by various inflammatory agents. Journal of Immunology 161 2873–2880.
69. Manna S, Gad Y, Mukhopadhyay A and Aggarwal B B (1999a) Suppression of tumor necrosis factor-activated nuclear transcription factor-kB, activator protein-1, c-Jun N-terminal kinase and apoptosis by b-lapachone. Biochemical Pharmacology 57 763–774.
70. Singh S, Natarajan K and Aggarwal B B (1996a) Capsaicin (8-methyl-N-vanillyl-6 nonenamide) is a potent inhibito of transcription factor NF-kB activation by diverse agents. Journal of Immunology 157 4412–4420.
71. Shrivastava A, Manna S K, Ray R, Aggarwal B B. (1998) Ectopic expression of hepatitis C virus core protein differentially regulates nuclear transcription factors. J Virol. 72 9722–8.
72. Toledano M B and Leonard W J (1991) Modulation of transcription factor NF-kB binding activity by oxidation-reduction in vitro. Proceedings of the National Academy of Sciences USA 88 4328–4332.
73. Singh S and Aggarwal B B (1995a) Protein tyrosine phosphatase inhibitors block tumor necrosis factor-dependent activation of the nuclear transcription factor NF-kB. Journal of Biological Chemistry 270 10631–10639.
74. Kumar A, Dhawan S and Aggarwal B B (1998) Emodin (3-methyl-1,6,8-trihydroxyanthaquinone) inhibits TNF-induced F-kB activation, IkB degradation, and expression of cell surface adhesion proteins in human vascular endothelial cells. Oncogene 17 913–918.
75. Natarajan K, Manna S K, Chaturvedi M M and Aggarwal B B (1998) Protein tyrosine kinase inhibitors block TNF-induced activation of NF-kB, degradation of IkBa, nuclear transcription of p65 and subsequent gene expression. Achives of Biochemistry and Biophysics 352 59–70.
76. Sun W H, Keller E T, Stebler B S, Ershler W B (1998) Estrogen inhibits phorbol ester-induced I-κβα transcription and protein degradation. Biochemical and Biophysical Research communications 244 691–695.
77. Pahl H L, Krauss B, Schulze-Osthoff K, Decker T, Traenckner E B, Vogt M, Myers C, Warning P, Mülbacher A, Czernilofsky A P and Baeuerle P A (1996) The immunosuppressive fungal metabolite gliotoxin specifically inhibits transcription factor NF-kB. Journal of Experimental Medicine 183 1829–1840.
78. Manna S K and Aggarwal B B (1999b) Immunosuppressive leflunomide metabolite (A77 1726) blockes TNF-dependent nuclear factor-kB activation and gene expression. Journal of Immunology 162 2095–2102.
79. Singh S, Darnay B G and Aggarwal B B (1996b) Site-specific tyrosine phosphorylation of IkBa negatively regulates its inducible phosphorylation and degradation. Journal of Biological Chemistry 271 31049–31054.
80. Mahboubi K, Young W, Ferreri N R. (1998) Tyrosine phosphatase-dependent/tyrosine kinase-independent induction of nuclear factor-kappa B by tumor necrosis factor-alpha: effects on prostaglandin endoperoxide synthase-2 mRNA accumulation. J Pharmacol Exp Ther. 285 862–8.
81. Hehner S P, Heinrich M, Borks P, Vogt M, Ratter F, Lehmann V, Schulze-Sthoff K, Droge W and Schmitz L (1998) Sesquiterpene lactones specifically inhibit activation of NF-kB by preventing the degradation of IkB-a and IkB-b. Journal of Biological Chemistry 273 1288–1297.
82. Bales K R, Du Y, Dodel R C, Yan G-M, Hamilton-Byrd E and Paul S M (1998) The NF-kB/Rel family of proteins mediates Ab-induced neurotoxicity and glial activation. Molecular Brain Research 57 63–72.

83. Auphan N, DiDonato J A, Rosette C, Helmberg A and Karin M (1995) Immunosuppression by glucocorticoids: inhibition of NF-kB activity through induction of IkB synthesis. Science 270 286–290.
84. Brostjan C, Anrather J, Csizmadia V, Stroka D, Soares M, Bach F H, Winkler H. (1996) Glucocorticoid-mediated repression of NFkappaB activity in endothelial cells does not involve 271 19612–6.
85. Ray A and Prefontaine K E (1994) Physical association and functional antagonism between the p65 subunit of transcription factor NF-kB and the glucocorticoid receptor. Proceedings of the National Academy of Sciences USA 91 752–756.
86. Scheinman R I, Gualberto A, Jewell C M, Cidlowski J and Baldwin Jr A S (1995) Characterization of mechanisms involved in transrepression of NF-kB by activated glucocorticoid receptors. Molecular and Cellular Biology 15 943–953.
87. Ehrlich L C, Hu S, Peterson P K and Chao C C (1998) IL-10 down-regulates human microglial IL-8 by inhibition of NF-kB activation. Neuroreport 9 1723–1726.
88. Lentsch A B, Shanley T P, Sarna V and Ward P A (1997) In vivo suppression of nuclear factor kB and preservation of IkBa by interleukin-10 and interleukin-3. Journal of Clinical Investigation 100 2443–2448.
89. Trepiccihio W L, Dorner A J, Interleukin-11 (1998) Interleukin-11 A gp130 cytokine. Annals of the New York Academy of Science 85612–21.
90. Rodriguez M S, Thompson J, Hay R T and Dargemont C (1999) Nuclear retention of IkappaBalpha protects it from signal-induced degradation and inhibits nuclear factor kappaB transcriptional activation. J Biol Chem 274 9108–9115.
91. Lin Y-C, Brown K and Siebenlist U (1995) Activation of NF-kB requires proteolysis of the inhibitor IkB-a: signal-induced phosphorylation of IkB-a alone does not release active NF-kB. Proceedings of the National Academy of Sciences USA 92 552–556.
92. Shoji S, Furuishi K, Ogata A, Yamataka K, Tachibana K, Mukai R, Uda A, Harano K, Matushita S and Misumi S (1998) An allosteric drug, o,o'-bismyristoyl thiamine disulfide, suppresses HIV-1 replication through prevention of nuclear translocation of both HIV-1 Tat and NF-kB. Biochemical and Biophysical Research Communications 249 745–753.
93. Le Page C, Sanceau J, Drapier J C, Wietzerbin J (1998) Inhibitors of ADP-ribosylation impair inducible nitric oxide synthase gene transcription through inhibition of NF-κβ activation. Biochemical and Biophysical Research Communications 243 451–457.
94. Gerbes A L, vollmar A M, Kiemer A K and Bilzer M (1998) The guanylate cyclase-coupled natriuretic peptide receptor: a new target for prevention of cold ischemia-reperfusion damage of the rat liver. Hepatology 28 1309–1317.
95. Bustos C, Hernandez-Presa M A, Ortego M, Tunon J, Ortega L, Perez F, Diaz C, Hernanadez G and Egido J (1998) HMG-CoA reductase inhibition by atorvastatin reduces neointimal inflammation in a rabbit model of atherosclerosis. Journal of the American College of Cardiology 32 2057–2064.
96. Hernandez-Presa M A, Bustos C, Ortego M, Tunon J, Ortega L and Egido J (1998) ACE inhibitor quinapril reduces the arterial expression of NF-kB-dependent proinflammatory factors but not of collagen I in a rabbit model of atherosclerosis. American Journal of Pathology 153 1825–1837.
97. Harant H, Wolff B and Lindley I J D (1998) 1a, 25-dihydroxyvitamin $D_3$ decreases DNA binding of nuclear factor-kB in human fibroblasts. FEBS Letters 436 329–334.
98. Miyanohara T, Ushikai M, Matsune S, Ueno K, Katahira S and Kurono Y (2000) Effects of clarithromycin on cultured nasal epithelial cells and fibroblasts. Laryngoscope 110 126–131.
99. Toledano M B and Leonard W J (1991) Modulation of transcription factor NF-kB binding activity by oxidation-reduction in vitro. Proceedings of the National Academy of Sciences USA 88 4328–4332.
100. Hiramoto M, Shimizu N, Sugimoto K, Tang J, Kawakami Y, Ito M, Aizawa S, Tanaka H, Makino I, Handa H (1998) Nuclear targeted suppresion of NF-κβ activity by novel quinone derivative E3330. Journal of Immunology 160 810–19.
101. Wang J Y, Guo J S, Li H, Liu S-L and Zern M A (1998) Inhibitory effect of glycyrrhizin on NF-kB binding activity in $CCl_4$-plus ethanol-induced liver cirrhosis in rats. Liver 18 180–185.
102. Iwasaki T, Uehara Y, Graves L, Rachie N and Bomsztyk K (1992) Herbimycin A blocks IL-1-induced NF-kB DNA-binding activity in lymphoid cell lines. FEBS Letters 298 240–244.
103. Mahon T M and O'Neill L A J (1995) Studies into the effect of the tyrosine kinase inhibitor herbimycin A on NF-kB activation in T lymphocytes. Evidence for a covalent modification of the p50 subunit. Journal of Biological Chemistry 270 28557–28564.
104. Bork P M, Bacher S, Schmitz M L, Kaspers U and Heinrich M (1999) Hypericin as a non-antioxidant inhibitor of NF-kB. Planta Med 65 297–300.
105. Pyatt D W, Stillman W S, Irons R D. (1998) Hydroquinone, a reactive metabolite of benzene, inhibits NF-kappa B in primary human CD4+ T lymphocytes. Toxicol Appl Pharimacol. 149 178–84.
106. Manna S K and Aggarwal B B (1999) Interleukin-4 downregulates both forms of TNF receptor and receptor-mediated apoptosis NF-kB, AP-1, c-Jun N-terminal kinase: comparison with interleukin-13. Journal of Biological Chemistry 273 33333–33341.
107. Powell P P, Dixon L K, Parkhouse R M. (1996) An IkappaB homolog encoded by African swine fever virus provides a novel mechanism for downregulation of proinflammatory cytokine responses in host macrophages. J Virol. 70 8527–33.
108. Revilla Y, Callejo M, Rodriguez J M, Culebras E, Nogal M L, Salas M L, Vinuela E and Fresno M (1998) Inhibition of nuclear factor kB activation by a virus-encoded IkB-like protein. Journal of Biological Chemistry 273 5405–5411.
109. Sueoka E, Sueoka N, Kai Y, Okabe S, Suganuma M, Kanematsu K, Yamamoto T and Fujiki H (1998) Anticancer activity of morphine and its synthetic derviative, KT-90, mediated through apoptosis and inhibition of NF-kB activation. Biochemical and Biophysical Research Communications 252 566–570.
110. Shumilla J A, Wetterhahn K E, Barchowsky A (1998) Inhibition of NF-κB binding to DNA by chromium. cadmium, mercury, zinc and aresente invitro: evidence of a thiol mechanism. Archives of Biochemistry and Biophysics 349 356–62.
111. Yang J, Merin J P, Nakano T, Kato T, Kitade Y and Okamoto T (1995) Inhibition of the DNA-binding activity of NF-kB by gold compounds in vitro. FEBS Letters 361 89–96.

112. Law R E, Stimmel J B, Damore M A, Carter C, Clarke S and Wall R (1992) Lipopolysaccharide-induced NF-kB activation in mouse 70Z/3 pre-B lymphocytes is inhibited by mevinolin and 5'-methylthioadenosine: roles of protein isoprenylation and carboxyl methylation reactions. Molecular and Cellular Biology 12 103–111.

113. Sugano N, Shimada K, Ito K and Murai S (1998) Nicotine inhibits the production of inflammatory mediators in U937 cells through modulation of nuclear factor-kB activation. Biochemical and Biophysical Research Communications 252 25–28.

114. Biswas D K, Dezube B J, Ahlers C M and Pardee A B (1993) Pentoxifylline inhibits HIV-1 LTR-driven gene expression by blocking NF-kB action. Journal of Acquired Immune Deficiency Syndromes 6 778–786.

115. Wang W, Tam W F, Hughes C C, Rath S and Sen R (1997) c-Rel is a target of pentoxifylline-mediated inhibition of T lymphocyte activation. Immunity 6 165–174.

116. Kotake Y, Sang H, Miyajima T and Wallis G L (1998) Inhibition of NF-kB, iNOS mRNA COX2 mRNA, and COX catalytic activity by phenyl-N-tert-butylnitrone (PBN). Biochimica et Biophysica Acta 1448 77–84.

117. Delgado M, Munoz-Elias E J, Kan Y, Gozes I, Fridkin M, Brenneman D E, Gomariz R P and Ganea D (1998) Vasoactive intestinal peptide and pituitary adenylate cyclase-activating polypeptide inhibit tumor necrosis factor a transcriptional activation by regulating nuclear factor-kB and cAMP response element-binding protein c-Jun. Journal of Biological Chemistry 273 31427–31436.

118. Kim C H, Kim J H, Moon S J, Chung K C, Hsu C Y, Seo J T and Ahn Y S (1999) Pyrithione, a zinc ionophore, inhibits NF-kappaB activation. Biochem Biophys Res Commun 259 505–509.

119. Fiedler M A, Wemke-Dollries K and Stark J M (1996) Inhibition of viral replication reverses respriatory syncytial virus-induced NF-kB activation and interleukin-8 gene expression in A549 cells. Journal of Virology 70 9079–9082.

120. Jin D-Y, Chae H Z, Rhee S G and Jeang K-T (1997) Regulatory role for a novel human thioredoxin peroxidase in NF-kB activation. Journal of Biological Chemistry 272 30952–30961.

121. Kawashima S, Hayashi M, Takii T, Kimura H, Zhang H L, Nagatsu A, Sakakibara J, Murata K, Oomoto Y and Onozaki K (1998) Serotonin derivative, N-(p-coumaroyl) serotonin, inhibits the production of TNF-a, IL-1a, IL-1b, and IL-6 by endotoxin-stimulated human blood monocytes. Journal of Interferon Cytokine Research 18 423–428.

122. Saliou C, Rihn B, Cillard J, Okamoto T and Packer L (1998) Selective inhibition of NF-kB activation by the flavinoid hepatoprotector silymarin in HepG2. Evidence for different activating pathways. FEBS Letters 440 8–12.

123. Oyama T, Ran S, Ishida T, Nadaf S, Kerr L, Carbone D P, Gabrilovich D I (1998) Vascular endothelial growth factor affects dendritic cell maturation through the inhibition of NF-κβ Activation in hemopoietic progenitor cells. Journal of Immunology 160 1224–32.

124. Gabrilovich D, Ishida T, Oyama T, Ran S, Kravtsov V, Nadaf S and Carbone D P (1998) Vascular endothelial growth factor inhibits the development of dendritic cells and dramatically affects the differentiation of multiple hematopoietic lineages in vivo. Blood 92 4150–4166.

125. Bergmann M, Hart L, Lindsay M, Barnes P J and Newton R (1998) IkBa degradation and nuclear factor-kB DNA binding are insufficient for interleukin-1b and tumor necrosis factor-a-induced kB-dependent transcription: requirement for an additional activation pathway. Journal of Biological Chemistry 273 6607–6610.

126. Qiu D, Zhao G, Aoki Y, Shi L, Uyei S A, Nazarian S, Ng JC-H and Kao PN (1999) Immunosuppressant PG490 (triptolide) inhibits T-cell interleukin-2 expression at the level of purine-box/nuclear factor of activated T-cells and NF-kB transcriptional activation. Journal of Biological Chemistry 274 13443–13450.

127. Sizemore N, Leung S and Stark G R (1999) Activation of phosphatidylinositol 3-kinase in response to interleukin-1 leads to phosphorylation and activation of the NF-kB p65/RelA subunit. Molecular and Cellular Biology 19 4798–4805.

128. Egan L J, Mays D C, Huntoon C J, Bell M P, Pike M G, Sandborn W J, Lipsky J J and McKean D J (1999) Inhibition of interleukin-1-stimulated NF-kB RelA/p65 phosphorylation by mesalamine is accompanied by decreased transcriptional activity. J Biol Chem 274 26448–26453.

129. Manna S K and Aggarwal B B (2000) Wortmannin inhibits activation of nuclear transcription factors NF-kappaB and activated protein-1 induced by lipopolysaccharide and phorbol ester. FEBS Lett 473 113–118.

What is claimed is:

1. A method for the treatment or reduction of mucositis comprising administering to an individual undergoing or preparing to undergo a treatment for cancer a therapeutically effective amount of a compound having the formula:

$$R_1 \diagup\!\!\!\diagdown \diagdown\!\!\!\diagup \sim\!\!\sim\!\!\sim \diagup\!\!\!\diagdown \diagdown\!\!\!\diagup R_4$$
$$\phantom{xxxxx} R_2 \phantom{xxxxxxxx} R_3$$

where $R_1$ and $R_4$ are OH, and $R_2$ and $R_3$ are independently OH or H, provided that when $R_1$ and $R_2$ are both OH, $R_1$ and $R_2$ cannot be disposed ortho to one another, and when $R_3$ and $R_4$ are both OH, $R_3$ and $R_4$ cannot be disposed ortho to one another.

2. The method of claim 1, wherein the treatment for cancer is radiation therapy.

3. The method of claim 1, wherein the treatment for cancer is chemotherapy.

4. The method of claim 1, wherein the mucositis is of the gastrointestinal tract.

5. The method of claim 4, wherein the mucositis is of the mouth, esophagus, or stomach.

6. The method of claim 1, wherein the compound is administered topically.

7. The method of claim 6, wherein the compound is administered in a rinse, troche, or gel.

8. The method of claim 1, wherein the compound is administered orally or by intraperitoneal injection.

9. The method of claim 1, wherein the compound is administered in a pharmaceutically acceptable carrier.

10. The method of claim 1, wherein the compound is resveratrol.

11. The method of claim 1, wherein the compound is cis.

12. The method of claim 1, wherein the compound is trans.

* * * * *